United States Patent [19]

Pirrung et al.

[11] Patent Number: 4,851,035

[45] Date of Patent: Jul. 25, 1989

[54] COMPOSITION FOR INHIBITION OF ETHYLENE PRODUCTION IN PLANTS

[75] Inventors: Michael C. Pirrung, Menlo Park, Calif.; Gerald M. McGeehan, Zurich, Switzerland

[73] Assignee: The Board of Trustees of the Leland Stanford Junior University, Stanford University, Stanford, Calif.

[21] Appl. No.: 858,444

[22] Filed: May 1, 1986

[51] Int. Cl.$^4$ .................... A61N 53/00; C07C 69/74; C07C 61/04; C07C 61/12

[52] U.S. Cl. ........................... 71/113; 71/67; 71/76; 71/77; 71/106; 71/118; 71/121; 560/118; 562/500; 564/152; 564/188; 564/217; 564/457

[58] Field of Search ................. 560/118; 71/106, 113, 71/68, 76, 77; 562/500

[56] References Cited

U.S. PATENT DOCUMENTS 3,117,987  1/1964  Horrom ........................ 560/118 X
4,317,834  3/1982  Fuchs ........................... 560/118 X
4,554,017  11/1985 Schroöder et al. ................. 71/76

OTHER PUBLICATIONS

Pirrung et al.; J. of Org. Chem. (1986), 51, pp. 2103–2106.
C.A. 104:109059t (1986); Pirrung et al.
Pirrung, J.A.C.S., 105 (1983), pp. 7207–7209.
Hoffman, et al., C.A., 97 (1982); 97:141787b.
Hoffman et al., Plant Physiol,. (1982) 70:195–199.

*Primary Examiner*—Joseph Paul Brust
*Attorney, Agent, or Firm*—Richard L. Neeley

[57] ABSTRACT

An ethylene biosynthesis inhibitor is provided comprising 2-cycloalkyl-1-aminocyclopropanecarboxylic acids or a derivative thereof. By applying the subject compound in an ethylene-production-inhibiting amount, ripening and senescence can be slowed. The compound finds use in conjunction with the inhibition of ripening and improved storage of fruits, vegetables and cut flowers.

11 Claims, No Drawings

COMPOSITION FOR INHIBITION OF ETHYLENE PRODUCTION IN PLANTS

BACKGROUND OF THE INVENTION

Field of the Invention

The problem of excessive crop ripening, which can result in spoilage and the short shelf life of fruits, vegetables and flowers, remains a continuous one. In growing crops, it is desirable that there be some control of the rate of ripening, so that ripening may be staggered or occur simultaneously, as desired. Once picked, the vegetable, fruit or flower should have a long shelf life and retain its organoleptic properties during that period. There is, therefore, substantial interest in finding ways which allow for the regulation of ripening and senescence in agricultural products.

It is known that 1-aminocyclopropane-carboxylic acid is an intermediate in the formation of ethylene, which is a part of the process of ripening. Therefore, if one could inhibit the formation of the 1-aminocyclopropanecarboxylic acid or its enzymatic transformation to ethylene, there would be an opportunity to modulate ethylene synthesis and modulate ripening.

BRIEF DESCRIPTION OF THE RELEVANT LITERATURE

Alkyl 1-aminocyclopropanecarboxylic acid derivatives (ACC derivatives) have been reported to require the trans stereochemistry to be processed by plant tissue (Hoffman et al., *Plant Physiol.* (1982) 70:195). The mechanism for ethylene production from ACC have been proposed (Pirrung, *J. Am. Chem. Soc.* (1983) 105:7207).

SUMMARY OF THE INVENTION

2-Cycloalkyl-1-aminocyclopropanecarboxylic acid (cycloalkyl ACC) formulations containing cycloalkyl ACC, and methods for using cycloalkyl ACC are provided to modulate the rate of ripening and senescence of agricultural products.

DESCRIPTION OF THE SPECIFIC EMBODIMENTS

2-Cyclopropyl-1-aminocyclopropanecarboxylic acid (cyclopropyl ACC) and the corresponding 2-cyclobutyl homologue (cyclobutyl ACC), as well as derivatives of both compounds, are provided for use in modulating the formation of ethylene in plants or plant parts, particularly produce, such as fruits, vegetables and ornamental flowers. Ripening, germination, senescence, and abscission may be modulated, providing for control of the rate of ripening during the growth period and moderation of the rate of ripening or the rate of senescence during storage.

Cyclopropyl and cyclobutyl ACC can be prepared in accordance with the method described by Schollkopf (Schollkopf et al., *Liebigs Ann. Chem.* (1973) 611). Methyl isocyanoacetate is condensed with (1',2'-dibromoethyl)cyclopropane to provide the desired biscyclopropane ring system. A two-step hydrolysis procedure and ion-exchange chromatography provide cyclopropyl ACC in high yield with a trans-cis ratio in excess of 7:1 in a mixture of sterioisomers. Recrystallization from 3:1 ethanol:water gives the pure trans isomer. Cyclobutyl ACC is prepared in the same manner from (1',2'-dibromoethyl)cyclobutane. In both cases, the intermediate 2-cycloalkyl-1-isocyanocyclo-propanecarboxylic acid ester is also a new compound. The intermediate can be hydrolyzed to the acid with aqueous base or to the amine with aqueous acid. The ester can be any hydrolyzable organic ester, if desired.

The major isomer of this synthetic route has the cyclopropyl group in the desirable configuration trans to the carboxyl group. Since the trans stereochemistry has been reported to be necessary for processing by plant tissue, the trans stereochemistry is preferred. Therefore, mixtures preferably have at least about 50% of the trans isomer and more preferably at least about 70% of the trans isomer.

The subject compounds may be employed as a single compound or derivative, or as a mixture of compounds, e.g., stereoisomers, and/or derivatives. Various derivatives may be prepared, where the amino groups may be derivatized by mono- or dialkylation by alkyl groups, preferably of from 1 to 4 carbon atoms; mono- or diacylation by acyl (alkanoyl) groups, preferably of from 1 to 4 carbon atoms, or combinations thereof, usually the substitutent being of from 1 to 2 carbon atoms.

The carboxyl group may be derivatized as a salt, particularly useful being physiologically acceptable salts such as ammonium or alkali metal salts (especially Li, Na, and K salts); esters, particularly alkyl groups of from 1 to 4 carbon atoms; and amides, which include the amino group, substituted amino groups (mono-or disubstituted by alkyl groups of from 1 to 4, usually 1 to 2, carbon atoms), and amino groups formed from a naturally occurring amino acid, e.g., glycine. Preferred naturally occuring amino acids are the genetically encoded amino acids. The cycloalkyl ACC can also be included as part of a polypeptide formed from naturally occurring amino acids, preferably a peptide of 5 or fewer amino acid residues or a peptide specifically transportable across plant membranes by a plant membrane transport system.

Generally, any hydrolyzable derivative of the amino or carboxylate group of the basic cycloalkyl ACC compound can be utilized since the active agent is believed to be the acid form. Water-soluble derivatives should be prepared for aqueous formulations while organic-solvent-soluble derivatives should be prepared for formulations used with organic solvents, such as oil sprays. All of the salt, amide, ester, and polypeptide derivatives mentioned herein are readily absorbed and transported by plants and plant parts. It is also possible to use the corresponding 2-cycloalkyl-1-aminocyclopropylmethanols, which are readily oxidized in plants to the corresponding carboxylic acids.

The subject compounds or compositions may be used for modulating ripening in plants by applying various formulations to plants or plant parts, such as produce, either during growth or after removal of a part from the plant. The method involves applying to the plant or plant part to affect plant growth and development, particularly ripening, an effective amount of a compound or composition according to the subject invention.

Applying a subject compound to a plant or plant part can occur in any manner that results in the compound reaching the plant part for which moderated ripening is desired. For example, a plant or plant part can be dipped into or sprayed with a solution or suspension of a subject compound. The plant or plant part may also take up a subject compound systemically. For example, cut flowers can be placed into a solution of a subject compound. It is also possible to delay ripening of a field crop by applying a subject compound to the plant or to the soil surface near the plant in the field. Application to the soil is not preferred since the subject compounds can be degraded by soil microorganisms, such as Pseudomonas.

Usually, the subject compound will be applied either neat or it will be formulated as a wet or dry powder, solution, or the like. Depending on the manner in which the subject compounds are employed, the concentration of the subject compounds in formulations may vary widely, usually being from 2–98% by weight of the formulation.

When supplied as concentrates for subsequent dilution or dispersion in various liquid media, the active ingredients may vary from about 2–98 weight percent, more usually from about 10–90 weight percent. In application to the plant or plant product, the active ingredient will normally vary from about 0.01 to 100 ppm, more usually from about 0.05 to 20 ppm, and frequently from about 0.1 to 10 ppm, based on the weight of the plant or plant part to which the active ingredient is being applied. These values are particularly useful for control of ripening, which results in formation of large amounts of ethylene. Smaller amounts are needed to moderate germination, senescense, or abscission, typically one-tenth or less of the stated amounts. All application amounts expressed in parts per million (ppm) refer to weights of active ingredient based on cyclopropyl ACC. Derivatives should be applied at a rate equivalent to this rate (e.g., a polypeptide with a molecular weight of 635, 5 times the molecular weight of cyclopropyl ACC, would be applied at 5 times the corresponding rate for cyclopropyl ACC).

A preferred method of application is as an aqueous spray. A typical aqueous cyclopropyl ACC formulation would contain approximately 400 mg/l of cyclopropyl ACC and would be used to spray a plant part until it is just wet (e.g., typically about 1 ml of the aqueous solution for a 300g pear). The same formulation can also be used as a wash solution in the preparation of fruits and vegetables for market, although lower concentrations (e.g., 10–50 mg/l) are also suitable for this purpose. The subject compounds and compositions should cause no problems for human consumption because of their close structural relationship to ACC, which occurs in relatively high concentrations in many foods, such as apples.

In addition to the active ingredients, compositions according to the subject invention can contain a carrier and/or surfactant, in addition to other materials which may be present, such as stabilizers, other agricultural reactive compounds, or the like.

The word "carrier" is intended to include both organic and inorganic, natural and synthetic materials, with which the subject active ingredients may be combined in order to facilitate its application to a plant or plant product. The carrier can be a solid, such as a clay, natural or synthetic silicate, resin, wax, inert powder or the like. The carrier can be a fluid, such as water, an alcohol, a ketone, a petroleum fraction, a chlorinated hydrocarbon, a liquefied gas, or a combination thereof.

Included in the formations can be emulsifers, dispersing agents, wetting agents, or mixtures thereof, which may be ionic, including anionic and cationic, or nonionic. Illustrative of various surface-active agents are salts of polyacrylic acids; salts of ligninsulphonic acids; condensates of ethylene oxide with fatty alcohols, fatty acids or fatty amines; fatty acids; fatty amines; and the like.

The compositions according to the subject invention can be prepared in the form of wettable powders, dusting powders, solutions, emulsifiable concentrates, emulsions, suspension concentrates, and aerosols. Active ingredients generally comprise from 2 to 98% by weight of the composition.

The wettable powders are usually prepared to contain from about 20–95 weight percent of active material and in addition to the solid carrier may include from 0–5 weight percent of a wetting agent, from 0–10 weight percent of a dispersing agent, and from 0–10 weight percent of one or more stabilizers and/or other adjuvants, such as penetrating agents, adhesives, anticaking agents, dyestuffs, and the like.

Particular materials which may find use include sodium isopropylnaphthalenesulfonate, sodium naphthalenesulfonate, sodium dodecylbenzenesulfonate, oxyethyleneated alyklphenol (where the alkyl group is from about 8 to 18 carbon atoms and the number of oxyethylene groups will vary from about 1 to 50, usually from about 5 to 20), silica, kaolin, Benomyl wettable powder, and the like. This list is not exhaustive, but rather illustrative of various compounds which have found extensive use in agricultural formulations.

Since ethylene acts as a ripening hormone in all known plants, there are no known limits on the plants or plant parts to which this invention can be applied. However, the invention is preferably practiced with agricultural products intended for human consumption and use in which spoilage during storage is a common problem, such as produce and fresh flowers. Examples of produce to which the invention is applicable include fruit, such as apples, peaches, pears, apricots, plums, oranges, limes, lemons, and figs, and vegetables, such as lettuce, cabbage, tomatoes, beans, peas, asparagus, carrots, and corn. Examples of flowers include roses, carnations, lilies, and orchids.

In addition to controlling ripening, subject compounds can be used to modulate the effects of ethylene at other times in a plant life cycle. Ethylene also acts as a plant hormone to speed germination of seed, senescence (wilting or other aging effects, such as the drying of grains and legumes in the fall), and abscission (natural fruit drop). Cycloalkyl ACCs can modulate all of these effects. For example, seed can be stored for longer times without sprouting if treated with subject compounds prior to storage. Fruit can be maintained on the plant, as can grain and legumes, until harvesting can take place at a later than normal time, either for convenience in harvesting or to extend the growing season. For example, senescence of soybeans (drying of the plants) could be delayed so that harvest could take place in late October or November rather than in September. When used to control senescence or abscission, subject compounds are preferably applied approximately five weeks prior to the normal harvest, although both earlier and later applications are still effective.

The invention now being generally described, the same will be better understood by reference to the following examples, which are not to be considered limiting of the invention unless so stated.

EXAMPLES

In order to demonstrate the effect of the subject compounds, the following study was performed. Carnations were treated with a formulation containing 0.8 mM cyclopropyl ACC in a formulation comprising deionized water, 2 mg/ml mannitol, and 50 μg/ml 8-hydroxyquinoline citrate (an antibiotic). Carnation blossom cuttings were placed in this solution which was shown to extend their lifetime by about 30%.

To demonstrate that 2-cyclopropyl ACC is an enzyme inhibitor, a Dixon analysis was conducted showing the inhibition of ethylene production in mung bean hypocotyl segments by the subject compounds ($I_{50}$ of 1.5 mM). In the assay, rates of ethylene production were measured for different concentrations of cyclopropyl ACC while maintaining a constant ACC concentration. The reaction was carried out in a sealed container fitted with a pierceable stopper through which gas samples could be taken by syringe. The assay mixture contained 20 segments of sprouted mung beans from which the heads and tail had been cut off (approximately 1 gram of plant tissue) in 2 ml deionized water containing 2 weight percent sucrose, 50 mM morpholineethanesulfuric acid buffer (pH 6.0), and 0.5 mM ACC. Inhibiter concentrations were varied from 0.25 to 16 mM.

Under similar incubation conditions with cyclopropyl ACC alone, samples were periodically removed and incubated with excess 1-aminocyclopropane carboxylic acid. Measurement of the rate of ethylene production (Yang and Yu, *Plant Physiol.* (1979) 64:1074) showed a decrease through time. A plot of inhibitor concentration versus ethylene production gave the value for $K_I$ (concentration at which 50% inhibition was shown). While not strictly first order, a $K_I$ could be estimated as $1.7 \times 10^{-5} s^{-1}$. Protection by excess ACC was demonstrated, but it was impossible to determine a partition ratio for the subject compound, since the yield of 1,4-pentadiene was low.

It is evident from the above results, that the subject compounds and compositions can be used for modulating growth of plants, particularly moderating the rate of ripening and senescence in plants and plant products. Thus, the subject compositions provide a new product which is particularly effective in improving yield and storage life of a wide variety of plant products.

All publications mentioned in this specification are indicative of the level of skill of those skilled in the art to which this invention pertains and are herein individually incorporated by reference in the locations in which they are cited equally as if each were stated individually to be so incorporated.

Although the foregoing invention has been described in some detail by way of illustration and example for purpose of clarity of understanding, it will be obvious that certain changes and modifications may be practices within the scope of the appended claims:

What is claimed is:

1. An ethylene-production-inhibiting compound of the formula

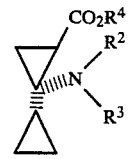

wherein
$R^2$ and $R^3$ independently represent H, a lower alkyl group, or a lower alkanoyl group; and $R^4$ represents H or an agronomically acceptable metal ion.

2. The compound of claim 1, wherein $R^4$ represents H, Li, Na, or K.

3. The compound of claim 1, wherein said compound is trans-2-cyclopropyl-1-aminocyclopropane-carboxylic acid.

4. A composition comprising a ripening regulating amount of compound of claim 1 and an agronomically acceptable carrier.

5. The composition of claim 4, wherein said composition contains from 2 to 98 weight percent of said compound.

6. A method of reducing the rate of ripening of a plant part, which comprises:
administering to a plant or plant part a ripening regulating amount of a compound of claim 1.

7. The method of claim 6 wherein said administering comprises applying said compound to a surface of said plant or plant part.

8. The method of claim 6 wherein said administering is accomplished by applying said compound at a rate of from 0.01 to 100 ppm active ingredient based on the weight of the plant or plant part to which said compound is applied.

9. A method of reducing the rate of germination of a seed, which comprises:
applying to a seed or to a plant in which said seed is being formed a germination regulating amount of a compound of claim 1.

10. A method of retarding abscission in a fruit-bearing plant, which comprises:
applying to said plant an abscission retarding amount of a compound of claim 1.

11. A method of retarding senescence of an agricultural product, which comprises:
applying to a plant part or plant a senescence retarding amount of a compound of claim 1.

* * * * *